United States Patent [19]

Correia et al.

[11] 3,947,508

[45] Mar. 30, 1976

[54] REMOVAL OF HCl BY DISTILLING A VINYL CHLORIDE FEED IN SOLUTION WITH AN ALCOHOL

[75] Inventors: Yves Correia; Jean-Claude Lanet, both of Saint-Auban, France

[73] Assignee: Rhone-Progil, Courbevoie, France

[22] Filed: June 3, 1974

[21] Appl. No.: 476,051

[30] Foreign Application Priority Data
June 20, 1973   France .............................. 73.22444

[52] U.S. Cl. ................. 260/652 P; 203/38; 203/55; 203/56; 203/63; 260/654 S; 260/656 AC
[51] Int. Cl.² ................... C07C 19/00; C07C 21/00
[58] Field of Search ....... 203/56, 55, 63, 67, 50–52, 203/28, 38; 260/654 S, 656 R, 656 AC, 652 P; 423/488, 481

[56] References Cited
UNITED STATES PATENTS

| | | | |
|---|---|---|---|
| 2,407,039 | 9/1946 | Stanley et al. ................. | 260/656 AC |
| 2,816,148 | 12/1957 | Anderson et al. ............ | 260/656 AC |
| 2,875,586 | 3/1959 | Pohl ................................ | 260/652 P |
| 3,244,755 | 4/1966 | Wofford .............................. | 203/38 |
| 3,278,397 | 10/1966 | Price ..................................... | 203/51 |
| 3,303,107 | 2/1967 | Locke ................................. | 203/38 |
| 3,470,230 | 9/1969 | Hirsch et al. .................... | 260/656 R |
| 3,655,787 | 4/1972 | Wiley ............................. | 260/652 P |

*Primary Examiner*—Norman Yudkoff
*Assistant Examiner*—Frank Sever
*Attorney, Agent, or Firm*—McDougall, Hersh & Scott

[57] ABSTRACT

Process for removing hydrochloric acid and other impurities which are contained in vinyl chloride monomer, by treatment in a distillation zone, comprising the addition to crude vinyl chloride, in the course of distillation thereof, of at least one alcohol selected from the group of $C_4$ to $C_{10}$ tertiary aliphatic alcohols and $C_3$ to $C_{10}$ primary or secondary alcohols with unsaturation in the alpha position, and rectifying the vinyl chloride monomer from the resulting mixture.

9 Claims, No Drawings

REMOVAL OF HCL BY DISTILLING A VINYL CHLORIDE FEED IN SOLUTION WITH AN ALCOHOL

The present invention concerns a process for removing hydrochloric acid from vinyl chloride monomer.

Vinyl chloride is produced, in most cases, by pyrolysis of 1,2-dichloroethane, in accordance with the known reaction:

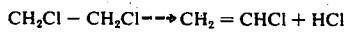

$$CH_2Cl - CH_2Cl \rightarrow CH_2 = CHCl + HCl$$

Separation by distillation of the hydrochloric acid leaves a crude vinyl chloride at the bottom of the column which is still acid and which is very difficult if not impossible to remove by distillation as the relative volatility of the acid with respect to the vinyl chloride diminishes rapidly as the amount of hydrochloric acid decreases. This amount of acid, although relatively small, of the order of from 1 to 20 parts per million by weight, cannot be tolerated since it is responsible for deficiencies which appear in vinyl chloride polymers, such as coloring and fish eyes.

It has previously been proposed that the small residual amounts of hydrochloric acid should be eliminated by passing the crude vinyl chloride over caustic soda, in solid form, or in aqueous solution.

However, this method suffers from serious disadvantages because it requires a special installation which is fairly substantial, both for operation and for maintenance thereof. Moreover, there is the danger of particles of caustic soda being entrained when the vinyl chloride passes at ambient temperature over the caustic soda.

The aim of the present invention is to overcome these disadvantages and thus to make it possible to produce vinyl chloride which is free from traces of acidity, without the necessity for a special installation, thereby simultaneously avoiding the problems of entrainment of caustic soda particles and handling of this corrosive substance.

According to the invention, to crude vinyl chloride containing hydrochloric acid, there is added, in the course of the distillation operations, at least one alcohol selected from the group of $C_4$ to $C_{10}$ primary or secondary alcohols with unsaturation in the alpha position.

Examples of alcohols with alpha-unsaturation include the following: allyl, propargyl, benzyl, furfuryl alcohols and 3-methyl 1-butyn-3-ol.

The above mentioned alcohols react very rapidly with the hydrochloric acid present, giving hydrocarbon chloride radicals and water which can be easily separated from the vinyl chloride, in accordance with the convention reaction:

$$ROH + HCl \rightarrow RCl + H_2O$$

in which R represents a $C_4$ to $C_{10}$ aliphatic hydrocarbon radical or a $C_3$ to $C_{10}$ aromatic, cycloaliphatic or aliphatic hydrocarbon radical.

Usually the crude vinyl chloride contains, as main impurities, hydrochloric acid (0.005 to 35.5% by weight), ethylene (up to 2.5% by weight), butadiene (0.001 to 0.01% by weight), methyl chloride (0.001 to 0.05% by weight), vinylidene chloride, cis and trans 1,2-dichloroethylene and 1,2-dichloroethane (giving a total of 0.01 to 1% by weight), and traces of water, phosgene and acetylene. The vinyl chloride is passed into a distillation zone (topping column) which removes the lightest components, essentially hydrochloric acid and ethylene, while the heavier substances which form the liquid residue at the bottom of the distillation column, essentially vinyl chloride, cis and trans dichloroethylenes, vinylidene chloride and dichloroethanes are introduced into a rectification zone (tailing column), in which the purified vinyl chloride monomer is collected at the column head while the heavier impurities are drawn off at the bottom of the column.

According to the invention, the alcohol is added to the crude vinyl chloride in the distillation zone.

In one embodiment of the invention, the alcohol, particularly when it is solid at ambient temperature, is first dissolved in an organic solvent which is chemically inert to the vinyl chloride monomer and which can be easily separated therefrom. The following can be mentioned inter alia as examples of the organic solvent, without the following list being considered as limiting on the invention: ethanol, dichloroethanes, 1,1,2-trichloroethane, perchloroethylene, trichloroethylene, carbon tetrachloride, tetrachloroethanes and/or pentachloroethane. The proportion of solvent to be used can vary within very wide limits. It can, for example, be between the amount which is just sufficient to dissolve the alcohol, to 100 to 200 times that amount by weight. However, there is no advantage in excessively diluting the alcohol since its reaction with hydrochloric acid is then slowed down and, in addition, the volume of liquid to be treated is increased without any benefit.

In a preferred embodiment of the invention, the alcohol is introduced into a zone which is located below the feed to the distillation zone, at the level of the zone of exhaustion of HCl and the other impurities more volatile than vinyl chloride. In practice, it is of advantage for the alcohol to be introduced into the lower half of the distillation zone.

The proportion of alcohol to be used depends on the amount of hydrochloric acid present in the crude vinyl chloride to be purified. Generally, it is necessary to add an amount which is at least equimolar relative to the amount of acid. However, there is no advantage in using too great an excess of alcohol, for example more than 10 times the equimolar amount of acid, as no advantage is gained from doing so.

The preferred alcohols of the invention are $C_4$ and/or $C_5$ saturated tertiary aliphatic alcohols.

Phosgene in the presence of traces of water has a tendency to undergo partial hydrolysis, giving an additional amount of hydrochloric acid, in accordance with the known reaction:

$$COCl_2 + H_2O \rightarrow CO_2 + 2HCl$$

The applicants have found that, under the operating conditions of the present invention, this reaction is slow relative to the reaction of esterification of the alcohol by hydrochloric acid.

Generally, the pressure in the distillation zone is such that the vinyl chloride is maintained in the liquified state, whereas the pressure in the rectification zone is such that the vinyl chloride is raised to boiling temperature. The pressure and the temperature used are selected within the respective ranges of from 1 to 20 bars and from $-13°$ to $+80°C$.

The following examples are given by way of illustration without limiting the invention.

EXAMPLE 1

Crude vinyl chloride containing the following impurities:

|  | % by weight |
|---|---|
| $C_2H_4$ | 0.750 |
| HCl | 2.500 |
| $CHCl=CHCl$ } | |
| $CH_2=CCl_2$ } | 0.700 |
| $H_2O$ | 0.001 |
| $COCl_2$ | 0.002 |
| $CH_2=CH-CH=CH_2$ | 0.005 |
| $C_2H_2$ | 0.0003 | is introduced at a rate of 18 tonnes per hour into a distillation zone formed of a distillation column operating at a pressure of 8 bars and at a column bottom temperature of approximately 57° C. After distillation, the column bottom contains a vinyl chloride containing the following impurities:

|  | % by weight |
|---|---|
| HCl | 0.0005 |
| $CHCl=CHCl$ } | |
| $CH_2=CCl_2$ } | 0.750 |
| $COCl_2$ | 0.0022 |
| $CH_2=CH-CH=CH_2$ | 0.0054 |
| $H_2O$ | 0.001 |

6 liters per hour of a solution of 0.7 kg of 2-methyl propan-2-ol in 5 liters of 1,2-dichloroethane, which corresponds to four times the molar amount of HCl to be removed, is then introduced into the lower third of the distillation column.

This topping column bottom substance supplies a rectification zone formed of a tailing column, which operates at a pressure of 8 bars, and a column bottom temperature of about 60°C. The vinyl chloride which is collected at the head of this column then contains only the following impurities, in very small amounts:

|  | % by weight |
|---|---|
| HCl | 0.00001 |
| $CH_2=CH-CH=CH_2$ | ≤ 0.0005 |
| $H_2O$ | 0.00015 |
| $CH_2=C-CH_3$ $\quad$ \| $\quad$ $CH_3$ | 0.00001 |

The isobutene

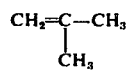

results from partial dehydration of the 2-methyl propan-2-ol, which is catalyzed by the HCl present.

By way of comparison, a test, identical to that of Example 1, was carried out, except that no 2-methyl propan-2-ol was incorporated in the crude vinyl chloride. It is found that, at the head of the rectification column, the vinyl chloride monomer collected still contains 5 parts per million by weight of HCl (0.0005% by weight), which represents 50 times more than in Example 1 which is carried out in accordance with the process of the invention.

EXAMPLE 2

A crude vinyl chloride, which contains the following main impurities:

|  | % by weight |
|---|---|
| $CH_2Cl-CH_2Cl$ | 0.300 |
| $CH_3Cl$ | 0.010 |
| $CH_2=CH-CH=CH_2$ | 0.005 |
| HCl | 30.000 |
| $C_2H_2$ | 0.0025 |
| $CHCl=CHCl$ } | |
| $CH_2=CCl_2$ } | 0.020 | is introduced into the distillation zone of Example 1, at a rate of 20 tonnes per hour.

The distillation column operates at a pressure of 7 bars and the temperature at the bottom of this column is 51°C.

After distillation, the bottom of the column contains a vinyl chloride having the following impurities:

|  | % by weight |
|---|---|
| $CH_2Cl-CH_2Cl$ | 0.500 |
| $CH_3Cl$ | 0.005 |
| $CH_2=CH-CH=CH_2$ | 0.008 |
| HCl | 0.002 |
| $CHCl=CHCl$ } | |
| $CH_2=CCl_2$ } | 0.030 |

2-methyl butan-2-ol is introduced into the lower quarter of the distillation column at a rate of 2 kg/hour which corresponds to an excess of 3 times the molar amount of HCl present.

This column bottom substance is then introduced into the same rectification zone as that used in Example 1, in which the pressure prevailing therein is 8 bars, while the temperature is 54°C.

At the head of the rectification column vinyl chloride is collected which then contains only the following impurities:

|  | % by weight |
|---|---|
| HCl | 0.00005 |
| $CH_2=CH-CH=CH_2$ | 0.0005 |
| $CH_3Cl$ | 0.0025 |

EXAMPLE 3

Example 1 described above was repeated, except that 2-methyl propan-2-ol was replaced by the same amount of benzyl alcohol. Results identical to those of Example 1 were obtained.

We claim:

1. In a process for removing hydrochloric acid and other impurities which are contained in crude vinyl chloride monomer, by treatment in a distillation zone, the improvement comprising, adding to the crude vinyl chloride at least one alcohol selected from the group consisting of $C_4$ to $C_{10}$ tertiary aliphatic alcohols and $C_3$ to $C_{10}$ primary and secondary alcohols with unsaturation in the alpha position, in a molar ratio equal to at least one mole of alcohol to one mole of hydrochloric acid, said alcohol reacting chemically with hydrochloric acid within said zone.

2. A process according to claim 1 in which the tertiary aliphatic alcohol is a saturated $C_4$ and/or $C_5$ alcohol.

3. A process according to claim 1 in which the $C_3$ to $C_{10}$ primary and $C_3$ to $C_{10}$ secondary alcohol with alpha unsaturation is selected from the group consisting of 3-methyl 1-butyn-3-ol, and allyl, propargyl, furfuryl and/or benzyl alcohols.

4. A process according to claim 1 in which the proportion of alcohol to be used is at least equimolar with respect to the amount of acid.

5. A process according to claim 1 in which the alcohol is dissolved, particularly when it is a solid, at ambient temperature, in an organic solvent which is chemically inert to the vinyl chloride monomer and which can be easily separated therefrom.

6. A process according to claim 5 in which the organic solvent is selected from the group consisting of ethanol, dichloroethanes, 1,1,2-trichloroethane, tetrachloroethanes, pentachloroethane, carbon tetrachloride, perchloroethylene and/or trichloroethylene.

7. A process according to claim 1 in which the alcohol is added to the crude vinyl chloride in the lower half of the distillation zone in which said distillation operation is carried out.

8. A process according to claim 1 in which the alcohol is added in a zone which is located below the feed to the distillation zone at the level of the zone of exhaustion in respect of HCl and said other impurities.

9. A process according to claim 8 in which the liquid residue from the distillation zone is subjected to distillation to separate a purified vinyl chloride monomer at the head.

* * * * *